(12) United States Patent
Christen

(10) Patent No.: US 7,138,148 B2
(45) Date of Patent: Nov. 21, 2006

(54) **USE OF EXTRACTS OF *GINKGO BILOBA* FOR PREPARING A MEDICAMENT INTENDED TO TREAT SARCOPENIA**

(75) Inventor: Yves Christen, Paris (FR)

(73) Assignee: Societe de Conseils de Recherches et d'Applications Scientifiques (SCRAS) (FR)

( * ) Notice: Subject to any disclaimer, the term of this patent is extended or adjusted under 35 U.S.C. 154(b) by 0 days.

(21) Appl. No.: 10/481,953

(22) PCT Filed: Jul. 16, 2002

(86) PCT No.: PCT/FR02/02519

§ 371 (c)(1),
(2), (4) Date: Dec. 22, 2003

(87) PCT Pub. No.: WO03/007973

PCT Pub. Date: Jan. 30, 2003

(65) Prior Publication Data

US 2004/0166180 A1    Aug. 26, 2004

(30) Foreign Application Priority Data

Jul. 17, 2001 (FR) .................................. 01 09506

(51) Int. Cl.
*A61K 36/16* (2006.01)
(52) U.S. Cl. ...................... 424/752; 514/907
(58) Field of Classification Search ................ 424/752
See application file for complete search history.

(56) References Cited

U.S. PATENT DOCUMENTS 4,571,407 A    2/1986 Chatterjee et al.
4,892,883 A *  1/1990 Chatterjee et al. .......... 514/464
6,030,621 A    2/2000 De Long et al.

FOREIGN PATENT DOCUMENTS

WO    WO 98/00024    1/1998

OTHER PUBLICATIONS

Punkt et al. Acta Histochemica. 1999. vol. 101, No. 1, pp. 53-69, CABA Abstract enclosed.*
Pitchumoni et al. J. Am. Geriatr. Soc. 1998. vol. 46, No. 12, pp. 1566-1572, DRUGU Abstract enclosed.*
Naphade, et al, Multimodal . . . Retrieval, XP 008001039, p. 188-195, 2001.
Chen, et al, Ginkgo . . . Cardiomyocytes, p. 5844, XP 8001027, 1998.
Yaku-N, XP-002193411, 1 page, 1999.
XP-002193410, Abstract- 1 pg, Skeletal . . . Aging, A. Navarro, et al, 2001.
XP-008001038 Nov. 1981, Arztezeitschfif fur Naturheilverfahren, 7 pages, 1981.
XP-008001026, Rapin, et al, Effects . . . Diabetic Rat, pp. 68-74, 1997.
XP-008001037, M. Allard, Traitement . . . Ginkgo biloba, pp. 1540-1545, 1986.

* cited by examiner

*Primary Examiner*—Christopher R. Tate
(74) *Attorney, Agent, or Firm*—Charles A. Muserlian

(57) ABSTRACT

The invention concerns the use of *Ginkgo biloba* extracts, and in particular *Ginkgo biloba* extracts comprising 20 to 30% of flavoneglycosides, 2.5 to 4.5% in total of gingkolides A, B, C and J, 2 to 4% of bilobalide, less than 10% of proanthocyanidins and at least 10 ppm of alkylphenol type compounds, for preparing a medicine for treating sarcopenia.

4 Claims, No Drawings

USE OF EXTRACTS OF *GINKGO BILOBA* FOR PREPARING A MEDICAMENT INTENDED TO TREAT SARCOPENIA

This application is a 371 of PCT/FR02/02519 filed Jul. 16, 2002.

The present Patent Application relates to the use of extracts of *Ginkgo biloba* for preparing a medicament intended to treat sarcopenia.

Sarcopenia is a muscular affection which effects most older people and manifests as a reduction in their muscle mass with age (cf. for example Chumlea et al., *Nutrition, Health & Aging*, 1(1), 7–12). Until now no satisfactory remedy has been found for this pathology.

In fact, if it has been shown for example that a treatment with growth hormone (GH) is capable of increasing the muscle mass, such a treatment, which is very expensive, presents some undesirable side effects (among which it could even be shortening the life expectancy of the subject treated).

The Applicant has now found that the administration of extracts of *Ginkgo biloba* allows prevention of sarcopenia or slowing down of its progression in the elderly subjects who already suffer from the disease.

The invention therefore relates primarily to the use of extracts of *Ginkgo biloba* for preparing a medicament intended to prevent sarcopenia or to slow down its progression in the elderly subjects who already suffer from the disease.

In fact, when, according to the invention, the elderly patient is treated with an extract of *Ginkgo biloba*, the relationship R equal to their muscle mass $M_m$ divided by their total body mass $M_t$ tends to remain stable or, in most cases, to increase. Preferably, the increase of R thus obtained after a treatment period of at least one month is greater than or equal to 5%, and more preferentially greater than or equal to 6 or even 8 or 10%.

The extracts of *Ginkgo biloba* which can be used according to the invention are such that they comprise at least flavoneglycosides and/or one or more ginkgolides. Preferably, the flavoneglycosides and/or the ginkgolide or ginkgolides are present at least up to a level of 25% by weight, more preferentially at least up to a level of 30% by weight and still more preferentially at least up to a level of 50% by weight in the extract of *Ginkgo biloba* used for preparing the medicament according to the invention.

Moreover, the proportion of compounds of alkylphenol type in the extract of *Ginkgo biloba* used according to the invention is preferably below 10 ppm, more preferentially below 5 ppm and still more preferentially below 1 ppm. If appropriate, the ginkgolide or the ginkgolides can be replaced by their acetylated homologues, their alkoxylated homologues or their glycosylated homologues (such as for example the compounds of general formula (I) described hereafter).

Preferably, the extract of *Ginkgo biloba* used for preparing a medicament according to the invention is enriched with flavoneglycosides and/or with ginkgolides. It can for example be an extract of type EGb 761®. According to another variant of the invention, the extract of *Ginkgo biloba* used for preparing a medicament according to the invention is any extract of *Ginkgo biloba* containing flavoneglycosides, ginkgolides and bilobalide, for example an extract of type CP 401.

By extract of type EGb 761®, is meant an extract with a composition approximately identical to that of the standardized extract EGb 761® as it has been defined in particular in the following article: K. Drieu, La presse médicale, 31, 25 Sep. 1986, supplement dedicated to the extract of *Ginkgo biloba* (EGb 761®), 1455–1457; or in the patents EP 431 535 and EP 431 536; by extract of type EGb 761®, is meant therefore in particular the extracts of *Ginkgo biloba* comprising from 20 to 30% of flavoneglycosides, from 2.5 to 4.5% in total of ginkgolides A, B, C and J, from 2 to 4% of bilobalide, less than 10% of proanthocyanidines and less than 10 ppm (preferably less than 5 ppm and still more preferentially less than 1 ppm) of compounds of alkylphenol type, preferably the extracts of *Ginkgo biloba* comprising from 22 to 36% of flavoneglycosides, from 2.5 to 3.5% in total of ginkgolides A, B, C and J, from 2.5 to 3.5% of bilobalide, less than 8% of proanthocyanidines and less than 10 ppm (preferably less than 5 ppm and still more preferentially less than 1 ppm) of compounds of alkylphenol type, and in particular the extracts of *Ginkgo biloba* comprising approximately 24% of flavoneglycosides, 3.1% in total of ginkgolides A, B, C and J, 2.9% of bilobalide, 6.5% of proanthocyanidines and less than 1 ppm of compounds of alkylphenol type.

By extract of type CP 401, is meant extracts such as those which are presented in the patent U.S. Pat. No. 5,389,370, in particular the extracts of *Ginkgo biloba* comprising from 5.5 to 8% in total of ginkgolides A, B, C and J, from 40 to 60% of flavoneglycosides and from 5 to 7% of bilobalide, preferably the extracts of *Ginkgo biloba* comprising from 6.5 to 7.5% in total of ginkgolides A, B, C and J, from 45 to 55% of flavoneglycosides and from 5.5 to 6.5% of bilobalide and quite particularly the extracts comprising approximately 7% in total of ginkgolides A, B, C and J, 50% of flavoneglycosides and 6% of bilobalide.

By extension, the extracts of type EGb 761® or CP 401 the ginkgolides of which have been replaced by their homologues of general formula (I) described later are also comparable with the extracts of type EGb 761® or CP 401.

According to a variant of the invention, at least one part of the ginkgolide or of the ginkgolides can be replaced by the compounds of general formula (I)

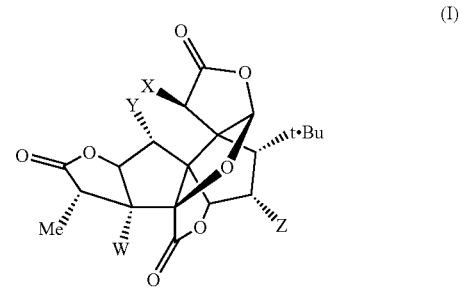

(I)

in which W, X, Y and Z independently represent the H, OH, linear or branched alkoxy or O-$G_S$ radicals, $G_S$-OH representing a mono- or a disaccharide, or one of their derivatives or analogues, it being understood that at least one of W, X, Y or Z represents an O-$G_S$ radical.

Preferably, the compounds of general formula (1) described previously are such that X represents an OH or O-$G_S$ radical, $G_S$-OH representing a mono- or a disaccharide, or one of their derivatives or analogues, and:

either W represents an OH or O-$G_S$ radical, Y represents H and Z represents H;

or W represents an OH or O-G$_S$ radical, Y represents an OH or O-G$_S$ radical and Z represents H;

or W represents an OH or O-G$_S$ radical, Y represents an OH or O-G$_S$ radical and Z represents an OH or O-G$_S$ radical;

or W represents an OH or O-G$_S$ radical, Y represents H and Z represents an OH or O-G$_S$ radical;

or W represents H, Y represents an OH or O-G$_S$ radical and Z represents an OH or O-G$_S$ radical;

or W represents an OH or O-G$_S$ radical, Y represents a linear or branched alkoxy radical and Z represents H.

For the preparation of the compounds of general formula (I), a person skilled in the art can refer to the PCT Patent Application WO 98/52959.

The pharmaceutical compositions comprising an extract of *Ginkgo biloba* can be in the solid form, for example powders, granules, tablets, gelatin capsules, liposomes, suppositories or patches. Appropriate solid supports can be, for example, calcium phosphate, magnesium stearate, talc, sugars, lactose, dextrin, starch, gelatin, cellulose, methyl cellulose, sodium carboxymethylcellulose, polyvinylpyrrolidine and wax.

The pharmaceutical compositions comprising an extract of *Ginkgo biloba* can also be presented in liquid form, for example, solutions, emulsions, suspensions or syrups. Appropriate liquids supports can be, for example, water, organic solvents such as glycerol or glycols, as well as their mixtures, in varying proportions, in water.

The administration of a medicament according to the invention can be carried out by topical, oral, or parenteral route, by injection (intramuscular, sub-cutaneous, intravenous, etc.), etc.

The envisaged daily administration dose of extract of *Ginkgo biloba* is comprised between 0.1 mg to 10 g according to the concentration of active ingredients in the extract and the severity of the sarcopenia of the subject. The definitive decision will be made by the attending doctor or veterinarian.

Unless they are defined otherwise, all the technical and scientific terms used here have the same meaning as that usually understood by a specialist familiar with the field to which this invention belongs. Similarly, all the publications, patent applications, all the patents and all other references mentioned here are incorporated by way of reference.

In order to show the advantage of the use of extracts of *Ginkgo biloba* as described previously in the treatment of sarcopenia, the test set out below can be carried out. Other tests which aim for example to determine the body composition and in particular the relationship between fat mass and non-fat mass (cf. Chumlea et al., *Nutrition, Health & Aging*, 1(1), 7–12) can also be carried out in order to achieve the same result.

Pharmacological Part

Comparative Measurement of the Growth of Body Weight and of the Mass of the Soleus Muscle in Rats:

Method 1

3 groups of rats are created: one group of 12 young Wistar rats (4 months) and two groups of old Wistar rats (22 months), one being constituted by 11 rats which receive normal drinking water for 5 weeks and the other being constituted by 12 rats which receive drinking water containing 75 mg per kg of standardized extract of *Ginkgo biloba* EGb 761®. After having been weighed, the young Wistar rats are sacrificed at the age of 4 months and 2 weeks while old Wistar rats are sacrificed at the age of 22 months and 3 weeks. In all the groups, the Plantaris muscles were weighed (muscles of the right side) and frozen for a typing analysis of the muscle fibres and of possible modifications of the mitochondrions (muscles of the left side).

The effect of the treatment in terms of the average increase in the weight of the Plantaris muscle in the treated rats compared to the untreated rats as well as the effect of the treatment in terms of an increase in the relationship of Plantaris muscle weight to total weight of the rat is determined.

Method 2

2 groups of 30 to 45 male rats of the Fischer 344 strain are constituted for the test. At the start of the test, the rats of the first group are aged 12 months and those of the second are aged 24 months.

Each of the groups of rats is divided into three sub-groups. The members of each first sub-group are treated with a daily dose of 100 mg/kg of EGb 761® administered per os; those of each second sub-group are treated with a daily dose of 50 mg/kg of EGb 761® administered per os; and finally those of each third sub-group do not receive any treatment. All the rats are weighed at the start of the treatment and their mass is recorded. After one month of treatment and living under the same conditions, the rats are weighed one last time before being sacrificed by decapitation. Their soleus muscles are then removed to be weighed.

The weight growth of the overall mass of the rats treated or not treated with EGb 761® are compared. The mass of the soleus muscles of the rats which are treated or not treated with EGb 761® are also compared. These comparisons allow the beneficial effect of the treatment with EGb 761® to be noted. In fact, the latter reduces the muscle loss linked to the age of the treated subject compared to the non-treated subject.

Results Obtained in the Case of Method 1:

The treated animals have gained less weight compared to the non-treated animals (the control group of old rats has gained +23% by weight in 5 weeks while the treated group of old rats has gained +13.5% by weight over the same period).

The measurements of the weight of the Plantaris muscles at the end of the study provide the following results:

| Young rats | Old non-treated rats | Old treated rats |
| --- | --- | --- |
| 334.63 ± 17.82 | 273.00 ± 16.12 | 296.50 ± 21.81 |

Finally, it is noted that the weight of the Plantaris muscles has increased by 8.60% in the treated rats compared to the non-treated rats while the relationship of the muscle weight with respect to the total weight has increased by 26.19% in the treated rats compared with the non-treated rats.

As a result, it can be seen that a treatment with extract of standardized *Ginkgo biloba* EGb 761® does allows reduction of the loss of muscle mass in the elderly subject.

The invention claimed is:

1. A method of treating sarcopenia in warm-blooded animals comprising administering to warm-blooded animals in need thereof an amount of an extract of *Ginkgo biloba* comprising from 20 to 30% of flavoneglycosides, from 2.5 to 4.5% in total of ginkgolides A, B, C and J, from 2 to 4% of bilobalide, less than 10% of proanthocyanidines and less than 10 ppm of compounds of alkylphenol type sufficient to treat sarcopenia.

2. The method of claim 1 wherein the extract of *Ginkgo biloba* comprises less than 5 ppm of compounds of alkylphenol type.

3. The method of claim 1 wherein the extract of Ginkgo biloba comprises a compound of the formula

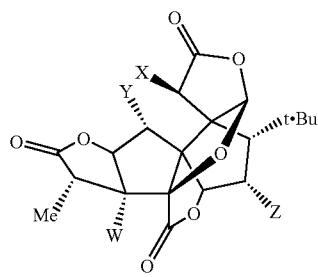

(I)

wherein W, X, Y and Z are independently selected from the group consisting of H, —OH, alkoxy and —O-$G_S$, $G_S$-OH being a mono- or a disaccharide, it being understood that at least one of W, X, Y or Z is —O-$G_S$.

4. The method of claim 3, wherein the compounds of formula (I) are such that X is OH or O-$G_S$, O-$G_S$-OH is a mono- or a disaccharide, and:

either W is OH or O-$G_S$, Y is H and Z is H;
or W is OH or O-$G_S$, Y is OH or O-$G_S$; and Z is H;
or W is OH or O-$G_S$, Y is OH or O-$G_S$ and Z is OH or O-$G_S$;
or W is OH or O-$G_S$, Y is H and Z is OH or O-$G_S$;
or W is H, Y is OH or O-$G_S$ and Z is OH or O-$G_S$;
or W is OH or O-$G_S$, Y is alkoxy and Z is H.

* * * * *